US008041095B2

(12) United States Patent
Mohamed et al.

(10) Patent No.: US 8,041,095 B2
(45) Date of Patent: Oct. 18, 2011

(54) METHOD AND APPARATUS FOR PRETREATMENT PLANNING OF ENDOVASCULAR COIL PLACEMENT

(75) Inventors: Ashraf Mohamed, Houston, TX (US); Marcus Pfister, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 798 days.

(21) Appl. No.: 12/136,862

(22) Filed: Jun. 11, 2008

(65) Prior Publication Data
US 2009/0310840 A1 Dec. 17, 2009

(51) Int. Cl.
G06K 9/00 (2006.01)
G06K 9/46 (2006.01)
G06K 9/52 (2006.01)
(52) U.S. Cl. ......... 382/131; 382/132; 382/181; 382/190
(58) Field of Classification Search ............... 382/131, 382/132, 181, 190
See application file for complete search history.

(56) References Cited

U.S. PATENT DOCUMENTS

| 6,975,973 | B1* | 12/2005 | Bruijns | 703/2 |
|---|---|---|---|---|
| 7,027,630 | B2* | 4/2006 | Bruijns | 382/131 |
| 7,194,117 | B2* | 3/2007 | Kaufman et al. | 382/128 |
| 7,379,574 | B2* | 5/2008 | Raman et al. | 382/128 |
| 7,865,001 | B2* | 1/2011 | Rongen et al. | 382/128 |
| 2005/0018885 | A1* | 1/2005 | Chen et al. | 382/128 |
| 2005/0147297 | A1* | 7/2005 | McLaughlin et al. | 382/171 |
| 2006/0184066 | A1* | 8/2006 | Karmonik et al. | 600/587 |
| 2009/0043187 | A1* | 2/2009 | Lautenschlager | 600/407 |
| 2009/0067568 | A1* | 3/2009 | Hall et al. | 378/4 |
| 2009/0088830 | A1* | 4/2009 | Mohamed et al. | 623/1.11 |
| 2009/0214097 | A1* | 8/2009 | Mohamed et al. | 382/131 |
| 2010/0309198 | A1* | 12/2010 | Kauffmann | 345/419 |

* cited by examiner

Primary Examiner — Allen C. Ho

(57) ABSTRACT

The present invention relates to a method and apparatus for pretreatment planning endovascular coil placement, comprising steps of: a) analyzing three-dimensional data enabling visualization of a volume of interest containing at least a part of a blood vessel with an aneurysm; b) determining the centerline of the vessel; c) determining the aneurysm diameter; d) determining the aneurysm dome height; e) creating a three-dimensional surface model of the aneurysm in the vessel, using the results from the previous steps; f) estimating the volume expansion of one or more coils with the aid of said surface model; and g) visual simulating at least one according to the estimated virtual coil being to place inside the aneurysm.

4 Claims, 5 Drawing Sheets

Different Coils C with different "Basket" Diameters

METHOD AND APPARATUS FOR PRETREATMENT PLANNING OF ENDOVASCULAR COIL PLACEMENT

FIELD OF THE INVENTION

The present invention relates to a method and apparatus for pretreatment planning of endovascular coil placement.

BACKGROUND OF THE INVENTION

An arterial aneurysm is a localized enlargement of an artery. Cerebral aneurysms or rather intracranial aneurysms (aneurysms of brain vessels), are "balloon-like" protrusion of intracranial arteries characterized by an opening ("neck") that feeds into an enlarged capsular structure ("dome").

The rupture of an intracranial aneurysm is a severe event that may potentially lead to severe disability or death.

Aneurysms (i.e. arterial malformations) especially in the brain are treated more and more by using minimal invasive approaches instead of open brain surgery. With reference to FIG. 1 a three-dimensional angiography of an aneurysm A in the brain is shown. It is possible, that the angiography is automatically processed to extract centerlines, diameters, aneurysm dome height etc. of the aneurysm and the surrounding vessels, in particular the parent vessel PV. With the minimal invasive approach, a catheter is brought through the arterial system of the patient to the aneurysm, through which small coils can be applied. The aneurysm is now treated by filling it subsequently with coils until the blood flow inside it is blocked and a thrombus is formed. Various types of coils are used for embolization of aneurysms including bare metal platinum and hydrocoils. It is advantageous that not only the aneurysm is sufficiently filled with coils to induce a thrombus, but also to ensure that the coils do not reach into the parent artery in order to minimize the risk of thrombosis formation inside the artery itself.

With reference to FIG. 2 an aneurysm A and the corresponding parent vessel PV is schematically shown. On the left hand side a) there is a view along the vessel, whereas on the right hand side b) there is a view from the side.

If the aneurysms neck N is not narrow, a stent is often placed to remodel the vessel end ensure that the coils stay inside the aneurysm.

According to US 2006/0184066 a method is used to support the previously mentioned stent placement. According to this method a surface model of an intracranial aneurysm in an artery is created, the aneurysm having a lumen, a neck and a dome. The method comprises steps of segmentation and analysis, in particular
computing centerline of the blood vessels and
aneurysm analysis like determining diameter and dome height.

With reference to FIG. 3 the above introduced information can be used to calculate properties of a virtual stent VS which optimally remodels the vessel. According to this information, a proper "real" stent can be chosen to treat the lesion.

Usually the coils form little baskets of different sizes (depending on the size of the coil, which is related to the highest curvature a coil can take). For larger aneurysms, multiple coils may have to be placed each one fitting into the previous placed coil. Therefore each aneurysm requires a careful choice of coils and the sequence of placement. For the treatment planning the physician has to decide which coils should be used in which order.

SUMMARY OF INVENTION

It is an objective of this invention to improve support for the afore mentioned pretreatment planning process.

Said problem is solved by the features mentioned in the independent claims. Preferred embodiments of the invention are described in the dependent claims.

A main aspect of the invention is a method for pretreatment planning of endovascular coil placement comprising the steps of:
a) analyzing three-dimensional data enabling visualization of a volume of interest containing at least a part of a blood vessel with an aneurysm to treat,
b) determining the centerline of the vessel,
c) determining the aneurysm diameter,
d) determining the aneurysm dome height,
e) creating a three-dimensional surface model of the aneurysm in the vessel, using the results from the previous steps,
f) estimating the volume expansion of one or more coils with the aid of said surface model,
g) visual simulating at least one according to step
f) estimated virtual coil being to place inside the aneurysm.

In the case that the aneurysm diameter and/or aneurysm dome height exceed a determined value more than one coil are proposed for placement. In other words: If a large aneurysm has to be treated, often several coils have to be placed one inside the previous one.

Further aspects of the invention are a computer system configured in any manner for performing the afore mentioned inventive methods and a computer storage device comprising machine readable and executable program instructions which comprise steps of performing the afore mentioned inventive methods.

The proposed invention provides the advantage that the physician automatically obtains proposals based on the analysis of three-dimensional angiography which coils should be used in which order to fill an aneurysm.

BRIEF DESCRIPTION OF THE DRAWINGS

Preferred embodiments of the present invention will now be described with reference to the accompanying drawings in which.

DETAILED DESCRIPTION OF THE DRAWINGS

Figure 1:
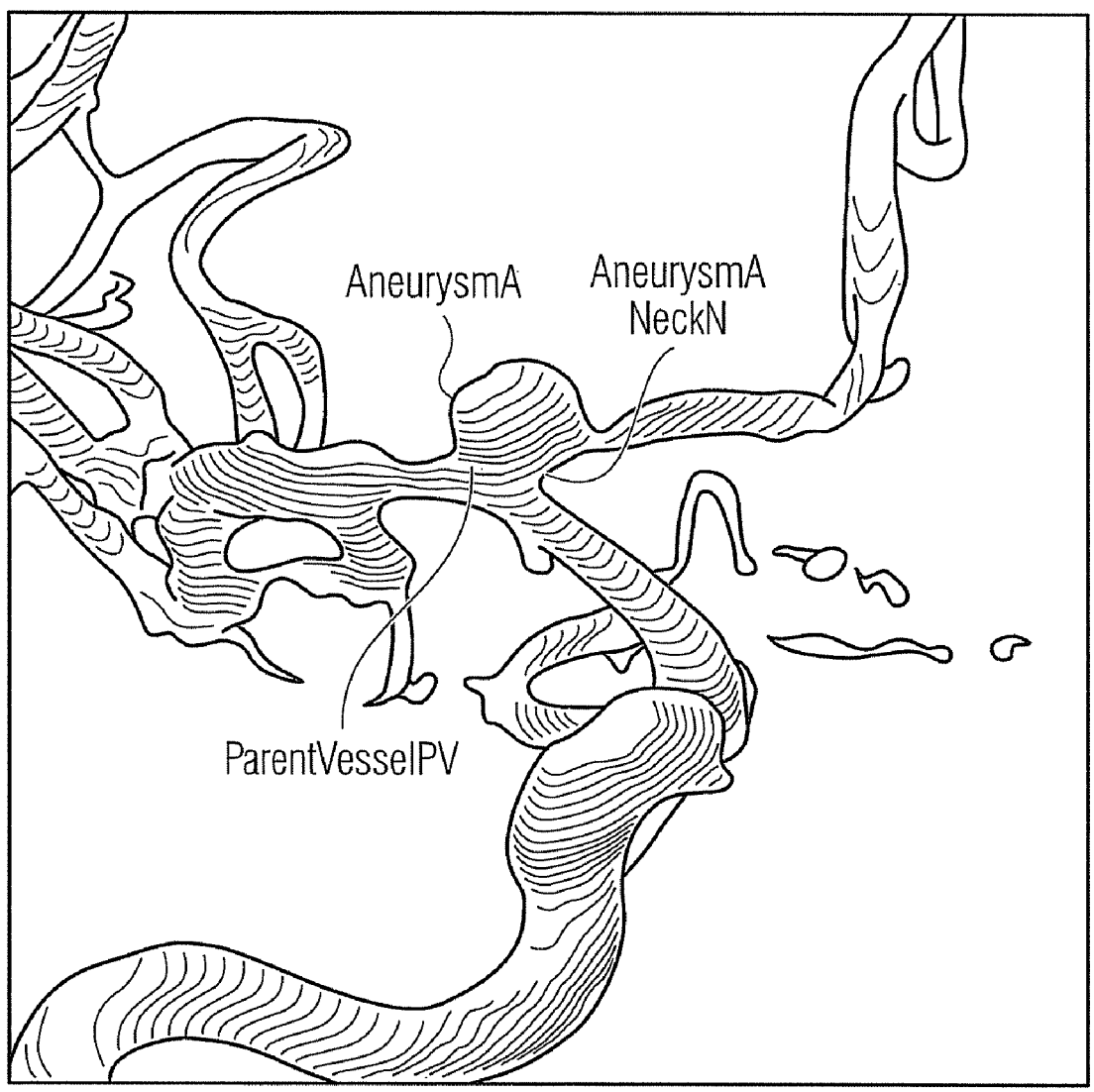
FIGS. 1 to 3 schematically shows the afore mentioned aneurysm and parent vessel, FIG. 4 schematically visualizes several virtual coils with different basket diameters and FIG. 5 schematically depicts an apparatus according to the invention.
Figure 2:
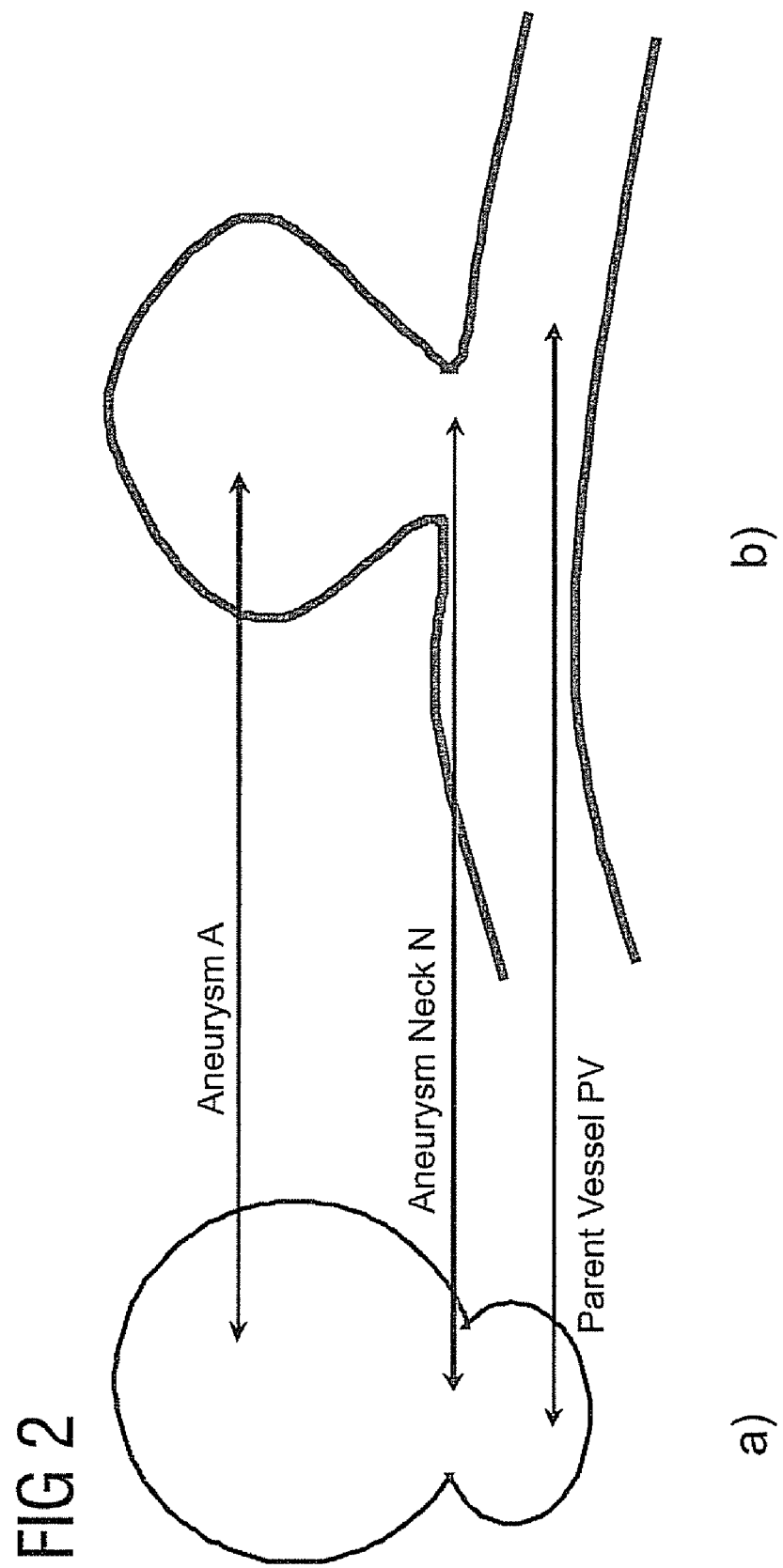
Figure 3:
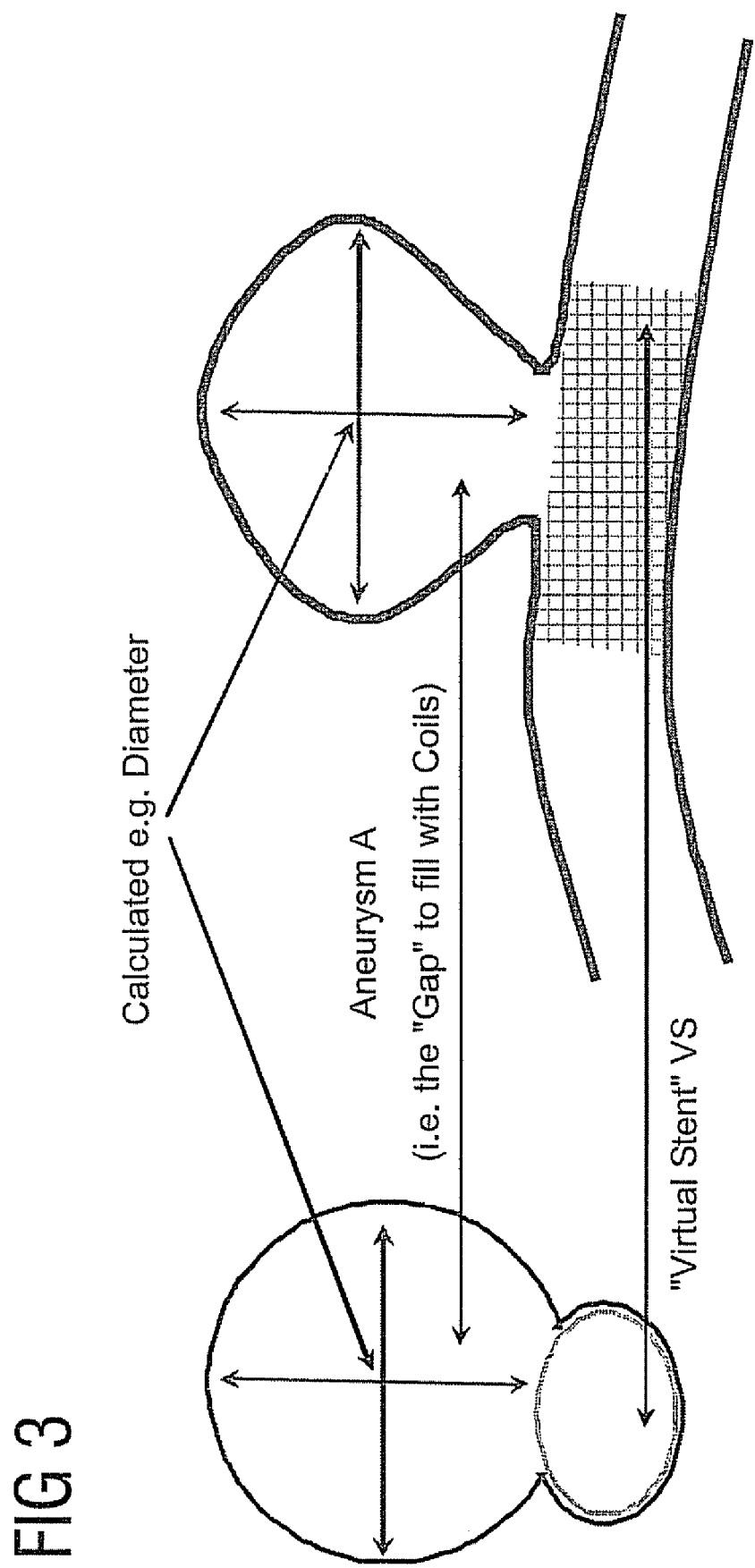
Figure 4:
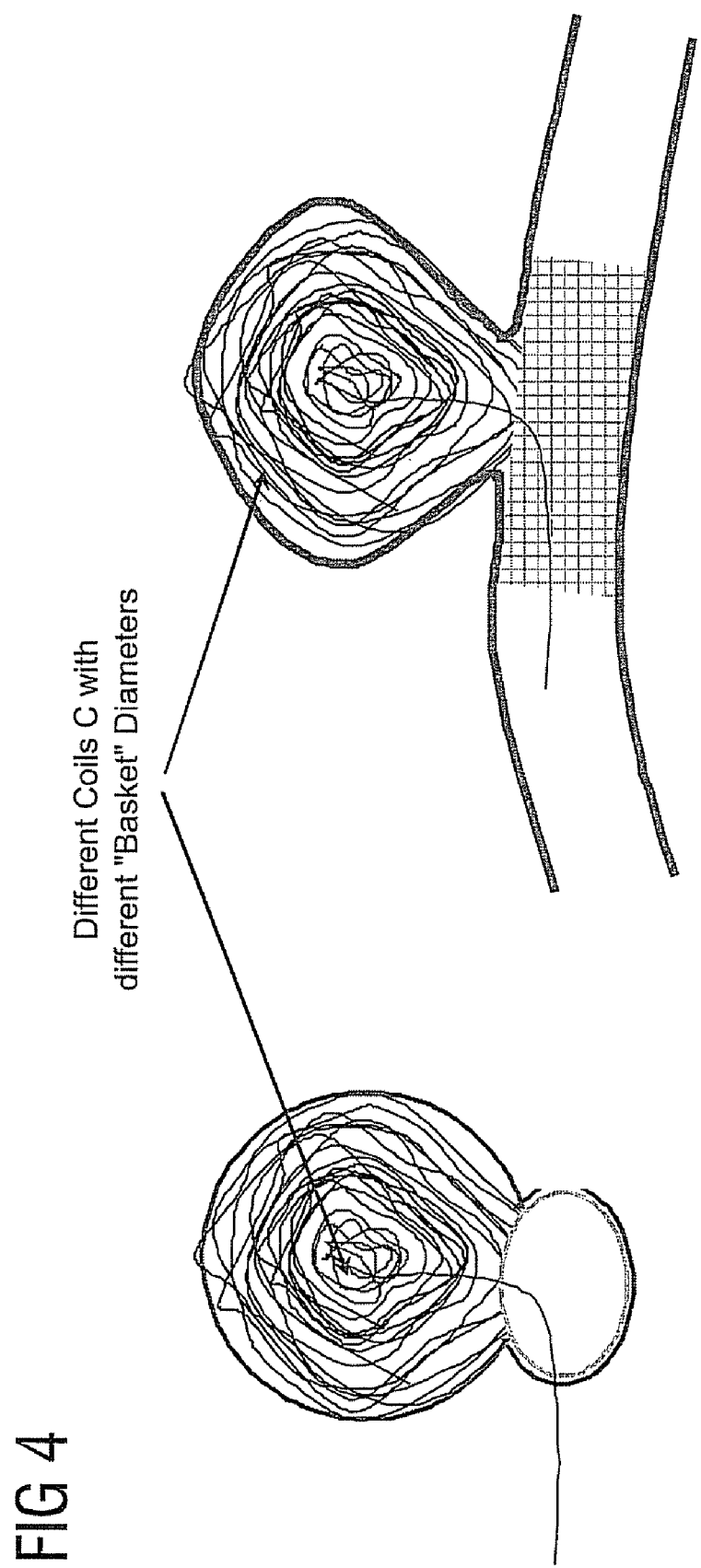

FIG. 4 schematically visualizes several virtual coils C with different basket diameters. Information obtained and/or extracted by a property calculation method e.g. according to US 2006/0184066 is used for a proposal which coil(s) in which order should be used to treat the aneurysm. Based on the knowledge of the behavior of different coils (i.e. "coil CXY forms a basket of X mm diameter leaving a gap of Y mm") and the knowledge of the size of the aneurysm, such a proposal can be provided. Based on this analysis, it can also be proposed which coils are to use, and in which order, if the aneurysm is too large for a single coil. According to the invention the "remaining" volume of the aneurysm (with or without a stent inside the parent vessel) is estimated for filling the aneurysm with one or more coils.

Figure 5:
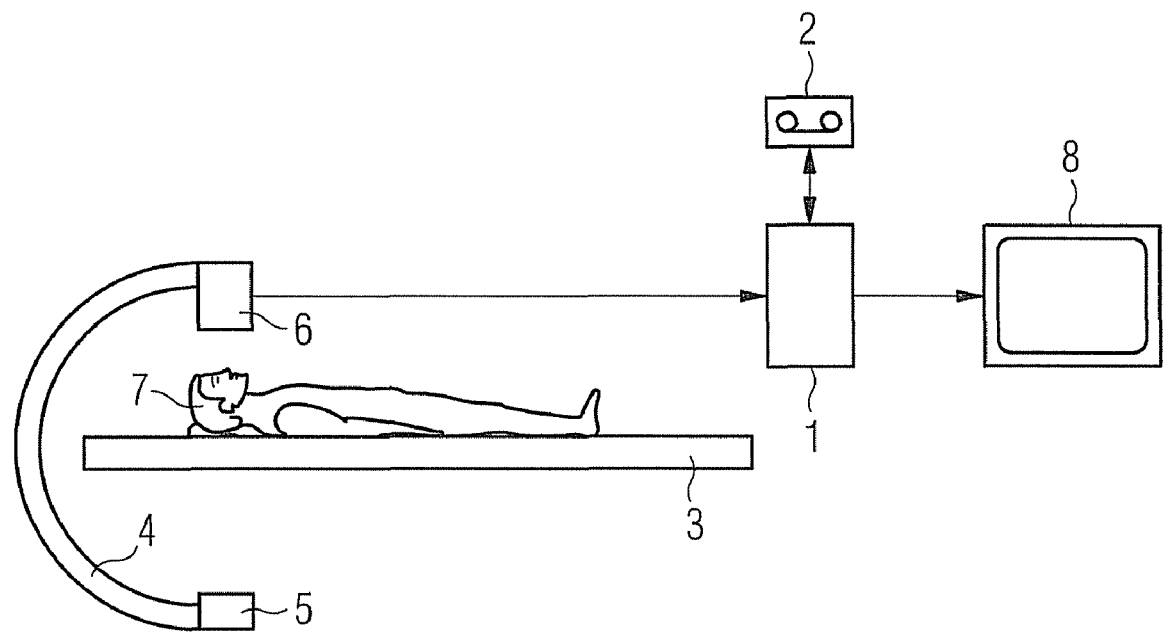

FIG. 5 schematically shows an apparatus according to the invention which comprises a system for performing the in the described inventive method.

With reference to FIG. 5 an apparatus, preferably a X-Ray apparatus, is shown. A surgical instrument (not shown in the figure) can be navigated through a vascular structure of a body volume (region of interest) of a patient 7. The system comprises a table 3 for supporting the patient and in the shown preferred embodiment it comprises a C-arm 4 with a X-ray source 5 and an image intensifier (or flat panel X-Ray detector) 6 for acquiring a series of images. The image intensifier (or flat panel X-Ray detector) is connected to a processing system 1, preferably a computer system, which can connect to a storage device 2 and a display unit 8. Software modules for performing the inventive method can be implemented in the processing system. The storage device can comprise an executable program of instructions to perform program steps for the afore described inventive methods.

Though the invention has been disclosed with reference to preferred embodiments, it will be understood by those skilled in the art that various changes in form and detail may be made without departing from the spirit and scope of the invention.

The invention claimed is:

1. A method for pretreatmently planning an endovascular coil placement on a computer, comprising:
   receiving a three-dimensional data of a volume of interest containing at least a part of a blood vessel with an aneurysm;
   determining a centerline of the vessel from the three-dimensional data;
   determining a diameter of the aneurysm from the three-dimensional data;
   determining a dome height of the aneurysm from the three-dimensional data;
   creating a three-dimensional surface model of the aneurysm based on the centerline of the vessel, the diameter of the aneurysm, and the dome height of the aneurysm;
   estimating a volume expansion of a coil to be placed inside the aneurysm based on the surface model of the aneurysm; and
   visually simulating the estimated coil.

2. The method as claimed in claim 1, wherein a plurality of coils are placed inside the aneurysm if the diameter of the aneurysm or the dome height of the aneurysm exceeds a determined value.

3. A non-transitory computer-readable storage medium executable on a computer for pretreatmently planning an endovascular coil placement, comprising:
   a computer program that:
      reads a three-dimensional data of a volume of interest containing at least a part of a blood vessel with an aneurysm,
      determines a centerline of the vessel from the three-dimensional data,
      determines a diameter of the aneurysm from the three-dimensional data
      determines a dome height of the aneurysm from the three-dimensional data,
      creates a three-dimensional surface model of the aneurysm based on the centerline of the vessel, the diameter of the aneurysm, and the dome height of the aneurysm,
      estimates a volume expansion of a coil to be placed inside the aneurysm based on the surface model of the aneurysm, and
      visually simulates the estimated coil.

4. A medical device for pretreatmently planning an endovascular coil placement, comprising:
   an image recoding device that records a three-dimensional data of a volume of interest containing at least a part of a blood vessel with an aneurysm; and
   a computer that:
      determines a centerline of the vessel from the three-dimensional data,
      determines a diameter of the aneurysm from the three-dimensional data,
      determines a dome height of the aneurysm from the three-dimensional data,
      creates a three-dimensional surface model of the aneurysm in the vessel based on the centerline of the vessel, the diameter and the dome height of the aneurysm,
      estimates a volume expansion of a coil to be placed inside the aneurysm based on the surface model, and
      visually simulates the estimated coil.

* * * * *